(12) United States Patent
Aliakbari et al.

(10) Patent No.: US 12,138,126 B2
(45) Date of Patent: Nov. 12, 2024

(54) DETECTING ELECTROMAGNETIC EMISSIONS ON ULTRASOUND SYSTEMS

(71) Applicant: FUJIFILM SONOSITE, INC., Bothell, WA (US)

(72) Inventors: Saeed Aliakbari, Snohomish, WA (US); Andrew Lundberg, Woodinville, WA (US); Davinder S. Dhatt, Woodinville, WA (US); Thomas Endres, Sagle, ID (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 161 days.

(21) Appl. No.: 17/737,746

(22) Filed: May 5, 2022

(65) Prior Publication Data

US 2023/0355215 A1    Nov. 9, 2023

(51) Int. Cl.
*A61B 8/08*    (2006.01)
*A61B 8/00*    (2006.01)
*G01R 31/00*    (2006.01)

(52) U.S. Cl.
CPC .............. *A61B 8/5269* (2013.01); *A61B 8/54* (2013.01); *G01R 31/001* (2013.01)

(58) Field of Classification Search
CPC ........ A61B 8/5269; A61B 8/54; G01R 31/001
See application file for complete search history.

(56) References Cited

U.S. PATENT DOCUMENTS

| | | | |
|---|---|---|---|
| 2002/0077627 A1* | 6/2002 | Johnson | A61B 18/18 606/41 |
| 2012/0065509 A1* | 3/2012 | Ziv-Ari | G01S 7/52077 600/443 |
| 2015/0025386 A1* | 1/2015 | Ninomiya | A61B 8/54 600/443 |
| 2015/0305712 A1* | 10/2015 | Urano | A61B 8/4455 600/443 |
| 2018/0333063 A1* | 11/2018 | Muchhala | G06N 3/047 |
| 2020/0082509 A1* | 3/2020 | Courtney | G01S 7/52077 |
| 2020/0088862 A1* | 3/2020 | Lundberg | G01S 7/5205 |
| 2021/0145393 A1* | 5/2021 | Gao | A61B 8/5269 |

FOREIGN PATENT DOCUMENTS

WO    WO-0243801 A2 *    6/2002    ............. A61B 6/463

* cited by examiner

*Primary Examiner* — Baisakhi Roy
*Assistant Examiner* — Kaitlyn E Sebastian
(74) *Attorney, Agent, or Firm* — Womble Bond Dickinson (US) LLP

(57) ABSTRACT

Systems and methods to detect electromagnetic (EM) emissions on ultrasound systems are described. In some embodiments, an ultrasound system includes an ultrasound scanner that is configured to generate ultrasound data based on reflections of ultrasound signals transmitted by the ultrasound scanner. An ultrasound machine is coupled to the ultrasound scanner and configured to generate an ultrasound image based on the ultrasound data. A circuit is coupled to the ultrasound machine and configured to make a determination whether the ultrasound image is corrupted by a noise process.

20 Claims, 9 Drawing Sheets

800

Generate sensor data indicative of an operating
environment within an ultrasound machine
801

↓

Generate, based on the sensor data, a report of
electromagnetic emissions within
the operating environment
802

↓

Determine, based on the sensor data, a
classification of the electromagnetic emissions
803

↓

Determine, based on the classification, a source
circuit of the electromagnetic emissions
within the ultrasound machine
804

↓

Disable the source circuit
805

↓

Enable an additional source circuit
that is redundant to the source circuit
806

FIG. 8

DETECTING ELECTROMAGNETIC EMISSIONS ON ULTRASOUND SYSTEMS

FIELD

Embodiments disclosed herein relate to ultrasound systems. More specifically, embodiments disclosed relate to detecting electromagnetic emissions on ultrasound systems.

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and can be rapidly deployed, ultrasound systems can be used in a variety of locations, such as in a care facility (e.g., in a patient's hospital room, an emergency department, etc.) and in the field (e.g., on the battlefield, at a triage center, remote communities, a patient's home, etc.). Some of these locations can include other medical devices, and to prevent the ultrasound systems from impacting the performance of these other medical devices, electromagnetic (EM) emissions from the ultrasound systems are regulated.

Conventional ultrasound systems rely on emulated environmental conditions and statistical inference to predict EM emissions through end-of-life (EOL). Traditionally, to meet regulatory compliance, the ultrasound systems are subjected to emulated environmental conditions, such as temperature cycles, vibration, shock, chemicals, humidity, and the like. EM emissions are then measured to statistically infer regulatory compliance over the life of the ultrasound system. However, this simulated approach does not guarantee that the ultrasound system will generate EM emissions that satisfy regulatory guidelines. Moreover, recent regulations require that ultrasound systems need to be compliant with EM emissions rules over the life of the ultrasound system, and this guarantee is simply not possible using the traditional approach of emulated environmental conditions and statistical inference.

If an ultrasound system fails to comply with regulatory guidelines, EM emissions can adversely affect the performance of medical equipment in proximity to the ultrasound system, such as an electrocardiogram (ECG) system, respirator, computer-controlled intravenous system, etc. In some situations, such as in the battlefield or at a triage center, an ultrasound system can be used on patients when the patient history is unknown. In these cases, if the patient has a medical implant, such as a pacemaker or cardioverter-defibrillator, the medical implant may not be known to the operator of the ultrasound system. Non-compliant EM emissions from the ultrasound system can leak onto the medical implant and alter the implant's performance, possibly in a catastrophic way. Accordingly, conventional ultrasound systems that cannot guarantee compliance with EM emissions guidelines over the entire life of the ultrasound system may not be suitable for use.

If an issue surrounding EM emissions is found once the ultrasound system is deployed, the ultrasound system is pulled out of service and sent for repair, resulting in a potential loss of care to the patient, extra cost to the caregiver and/or the manufacturer, and potential damage to the brand for the manufacturer.

SUMMARY

Systems and methods to detect electromagnetic (EM) emissions on ultrasound systems are described. In some embodiments, an ultrasound system includes an ultrasound scanner that generates ultrasound data based on reflections of ultrasound signals transmitted by the ultrasound scanner. An ultrasound machine is coupled to the ultrasound scanner and generates an ultrasound image based on the ultrasound data. A circuit coupled to the ultrasound machine makes a determination as to whether the ultrasound image is corrupted by a noise process.

In some embodiments, an ultrasound machine includes an image processor that generates an ultrasound image based on ultrasound data received from an ultrasound scanner as part of an ultrasound examination. At least one sensor is coupled to the image processor and generates, during the ultrasound examination, sensor data indicative of an operating environment within the ultrasound machine. A circuit is coupled to the at least one sensor and generates, during the ultrasound examination and based on at least one of the sensor data and the ultrasound image, a probability that the ultrasound image includes artifacts from electromagnetic emissions.

In some embodiments, a method is implemented by an ultrasound system that involves generating an ultrasound image as part of an ultrasound examination and generating, during the ultrasound examination and with a sensor implemented at least partially in hardware of the ultrasound system, sensor data indicative of electromagnetic emissions. The method also includes generating, during the ultrasound examination, with a neural network implemented at least partially in hardware of the ultrasound system, and based on at least one of the ultrasound image and the sensor data, a probability that the ultrasound image includes artifacts from the electromagnetic emissions.

Other systems, machines and methods to detect EM emissions on ultrasound systems are also described.

BRIEF DESCRIPTION OF THE DRAWINGS

The appended drawings illustrate examples and are, therefore, exemplary embodiments and not considered to be limiting in scope.

FIG. 8 is a data flow diagram of a process for an ultrasound system to detect electromagnetic emissions according to some embodiments.

DETAILED DESCRIPTION

Figure 1:
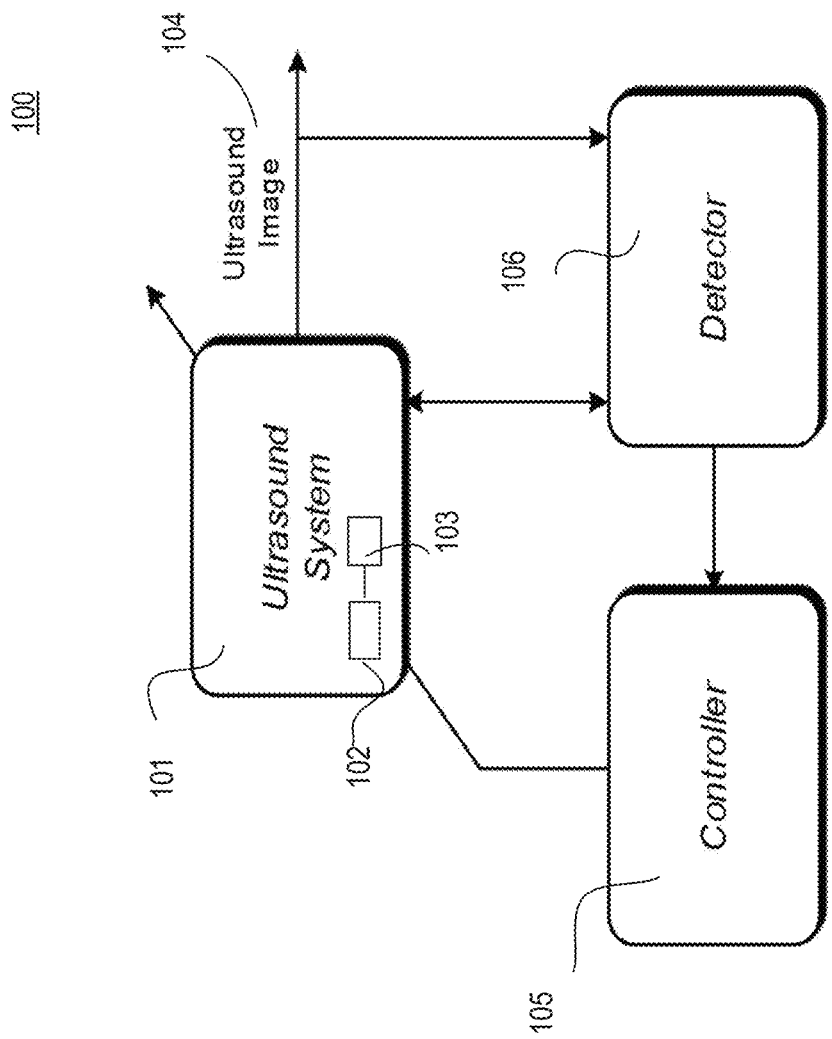
FIG. 1 is a view of a system to detect EM emissions according to some embodiments.

Systems and methods to detect electromagnetic (EM) emissions on ultrasound systems are described. In some embodiments, an ultrasound system includes an ultrasound scanner that generates ultrasound data based on reflections of ultrasound signals transmitted by the ultrasound scanner. An ultrasound machine is coupled to the ultrasound scanner and generates an ultrasound image based on the ultrasound data. A circuit is coupled to the ultrasound machine and makes a determination as to whether the ultrasound image is corrupted by a noise process.

In the following description, numerous details are set forth to provide a more thorough explanation of embodiments of the invention. It will be apparent, however, to one of ordinary skill in the art, that embodiments of the invention may be practiced without these specific details. In other instances, well-known structures and devices are shown in block diagram form, rather than in detail, in order to avoid obscuring embodiments of the present invention.

Various embodiments and aspects will be described with reference to details discussed below, and the accompanying drawings will illustrate the various embodiments. The following description and drawings are illustrative and are not to be construed as limiting. Numerous specific details are described to provide a thorough understanding of various embodiments. However, in certain instances, well-known or conventional details are not described in order to provide a concise discussion of embodiments.

Reference in the specification to "one example", "an example", "one embodiment" or "an embodiment" means that a particular feature, structure, or characteristic described in conjunction with the embodiment can be included in at least one embodiment. The appearances of the phrases "in one embodiment" or "in an embodiment" in various places in the specification do not necessarily all refer to the same embodiment. The processes depicted in the figures that follow are performed by processing logic that comprises hardware (e.g., circuitry, dedicated logic, etc.), software, firmware, or combinations thereof. Although the processes are described below in terms of some sequential operations, it should be appreciated that some of the operations described may be performed in a different order. Moreover, some operations may be performed in parallel rather than sequentially.

In the specification, the term "and/or" describes that three relationships between objects may exist. For example, A and/or B may represent the following cases: only A exists, both A and B exist, and only B exists, where A and B may be singular or plural.

Conventional ultrasound systems that use emulated environmental conditions and statistical inference to determine EM emissions cannot guarantee regulatory compliance over the entire life of the ultrasound systems. Therefore, these conventional ultrasound systems can be unsuitable for operation because they can influence medical systems in proximity to the ultrasound systems and can interfere with medical implants. Accordingly, systems, devices, and techniques are described herein for detecting EM emissions in ultrasound systems. In some cases, the ultrasound system can detect EM emissions and implement a correction to reduce the EM emissions.

Usually, ultrasound systems implement hardware to reduce the amount of EM emissions caused by the ultrasound systems, such as Faraday cages in the chassis of the ultrasound system, shields over integrated circuits (IC's) and/or printed circuit boards (PCBs), cable shielding, ground clamps, and the like. However, if one or more of these hardware solutions fail, which can be common throughout the use of the ultrasound system, EM emissions from the ultrasound system can be increased to the point that the ultrasound system fails to meet regulatory guidelines. As an example, the regulatory guidelines can include a spectral mask that defines allowable levels of EM emissions, and a hardware failure in the ultrasound system can result in spurious frequency emissions that exceed the allowable levels.

FIG. 1 is a view 100 of a system to detect EM emissions according to some embodiments. As shown in FIG. 1, the system includes an ultrasound system 101, a controller 105 and a circuit that includes a detector 106. Ultrasound system 101 includes an ultrasound scanner 102 and an ultrasound machine 103. The ultrasound scanner 102 can include an ultrasound probe and/or transducer array configured to transmit and receive ultrasound signals. Ultrasound machine 103 includes a processor that generates ultrasound data based on reflections of ultrasound signals transmitted by the ultrasound scanner 102. In some embodiments, ultrasound machine 103 includes an image processor that generates an ultrasound image 104 based on ultrasound data received from the ultrasound scanner 102 as part of an ultrasound examination. In some embodiments, the circuit including detector 106 makes a determination as to whether the ultrasound image is corrupted by a noise process. Additionally or alternatively, detector 106 can determine a level of EM emissions and/or whether EM emissions are at acceptable levels. The detector can automatically determine whether a noise process (e.g., EM emissions, or another noise process) is at is at an acceptable level and the controller 105 can take a corrective action to reduce the noise process prior to and/or during using the ultrasound system. Controller 105 can take one or more actions in response to EM emissions determined by the detector 106. The detector and controller can be configured in any suitable way. In some embodiments, the detector 106 and controller 105 are implemented in a feedback control loop to, in some cases, automatically detect EM emissions and implement a correction, as illustrated in FIG. 1. Detector 106 can implement any circuit (e.g., hardware, software, firmware, or combinations thereof) to determine a property of EM emissions. In some embodiments, detector 106 is a direct detector that directly measures EM emissions. In some embodiments, the direct detector includes at least one sensor that generates, during an ultrasound examination, sensor data indicative of an operating environment within the ultrasound machine. In at least some embodiments, the sensor data includes at least one of an amount of RF content, an impedance, a temperature, pressure sensor data (e.g., a torque, other pressure data, etc.), a strain, and an amount of light. In some embodiments, the circuit coupled to the processor generates, during the ultrasound examination and based on at least one of the sensor data and the ultrasound image, a probability that the ultrasound image includes artifacts from electromagnetic emissions. In some embodiments, the circuit generates the probability that the ultrasound image includes artifacts from electromagnetic emissions based on a comparison of the ultrasound image and an additional ultrasound image that lacks the artifacts from electromagnetic emissions. In some embodiments, based on the probability that the ultrasound image includes artifacts from electromagnetic emissions, controller 105 takes a corrective action to reduce the electromagnetic emissions.

In some embodiments, the detector 106 includes an indirect detector that indirectly measures EM emissions by measuring a property or artifact of the ultrasound system and inferring an amount of EM emissions from the measured property or artifact. In some embodiments, the detector 106 includes a classifier (not shown) that classifies EM emissions according to type, e.g., spurious, broadband, burst noise, and other types of noises. The classifier can also generate a description of the frequency content.

In some embodiments, the circuit of the detector 106 makes a determination as to whether the ultrasound image is corrupted by a noise process based on the sensor data and the ultrasound image data (e.g., the ultrasound image 104). In some embodiments, the circuit of the detector 106 makes a determination as to whether a noise process is present in the ultrasound system 101 based on at least one of the sensor data and the ultrasound image data (e.g., the ultrasound image 104).

Examples of Direct Detectors

Direct detectors directly measure EM emissions, and can include any suitable type of sensor, for example, an RF receiver, or a sensor circuit that outputs one or more signals indicative of the content of the EM emissions. In some embodiments, the direct detector includes an antenna coupled to a circuit that measures a signal amplitude, a power, or both the signal amplitude and power over one or more frequencies. In some embodiments, a location of the antenna of the direct detector is determined based on a location of a likely source of EM emissions. For example, the antenna of the direct detector can be placed in close proximity of the likely source of EM emission. The circuit of the direct detector can include any suitable components. In some embodiments, the circuit of the direct detector includes a tunable oscillator and a mixer that multiplies a signal from the antenna with a signal from the oscillator. The spectral content of the EM emissions can be determined from the output of the mixer and the frequency of the tunable oscillator.

For example, if the EM emissions include a frequency component at the frequency of the oscillator, a DC component will be generated at the output of the mixer. The power of the EM emissions can be determined from the amplitude of the DC component. By varying (e.g., sweeping) the frequency of the oscillator, the direct detector can determine the spectral content of the EM emissions over a range of frequencies. In at least some embodiments, the circuit of a direct detector includes one or more transistors, diodes, inductors, and/or operational amplifiers arranged to generate a signal indicative of the EM emissions. The circuit of the direct detector can include one or more variable resistors to change their resistance to determine the spectral content of the EM emissions. In some embodiments, the direct detector includes an analog-to-digital converter (ADC) that digitizes a signal from an RF-sensing antenna and circuitry to perform a fast Fourier transform (FFT). By applying the FFT to an output of the ADC, the direct detector can determine the spectral content of the EM emissions. In some embodiments, the direct detector includes at least one antenna coupled to a downconverter, and/or ADC, FFT and an RF sensor.

Examples of Indirect Detectors

Indirect detectors indirectly measure EM emissions by measuring a property or signal of the ultrasound system or an output of the ultrasound system, and inferring an amount of EM emissions, a type of EM emissions, or both the amount and type of EM emissions based on the measured property and/or signal. An indirect detector can include one or more of the following: a circuit to measure an impedance of a grounding mechanism, a sensor (e.g., an accelerometer) that counts the number of times that a display monitor device is opened and closed (e.g., the number of the monitor open/close cycles) to provide a usage parameter associated with a failure mechanism, and one or more neural networks to determine presence and type of EM emissions from an ultrasound image, as described in further detail below. In at least some embodiments, the indirect detector includes one or more processors and a memory coupled to the processor to perform methods to detect EM emissions on ultrasound systems as described herein.

Figure 2:
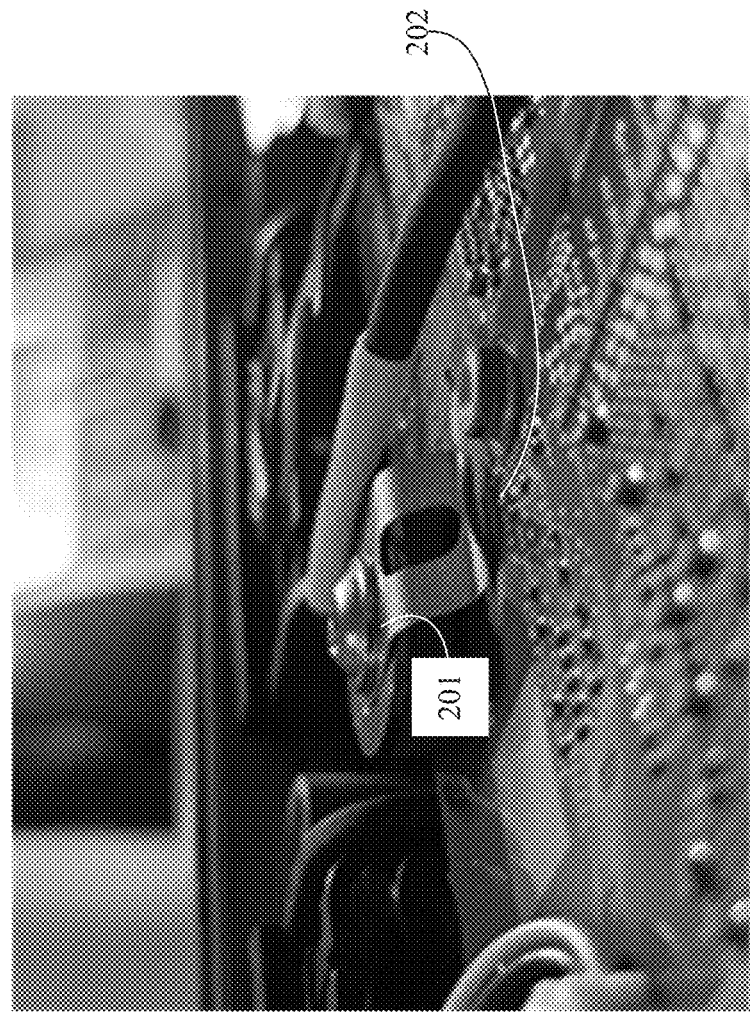
FIG. 2 is a view of an ultrasound system that includes a ground spring clip to ensure proper grounding and reduce EM emissions according to some embodiments.

FIG. 2 is a view 200 of an ultrasound system that includes a ground spring clip 201 to ensure proper grounding and reduce EM emissions according to some embodiments. Referring to FIG. 2, during initial assembly or use of the ultrasound system (e.g., due to mechanical shock), ground spring clip 201 can loosen and fail to make sufficient contact with a ground pad 202 on a printed circuit board (PCB) of the ultrasound system. In this case, the impedance between ground spring clip 201 and ground pad 202 is increased, and EM emissions can leak from the ultrasound system.

Figure 3:
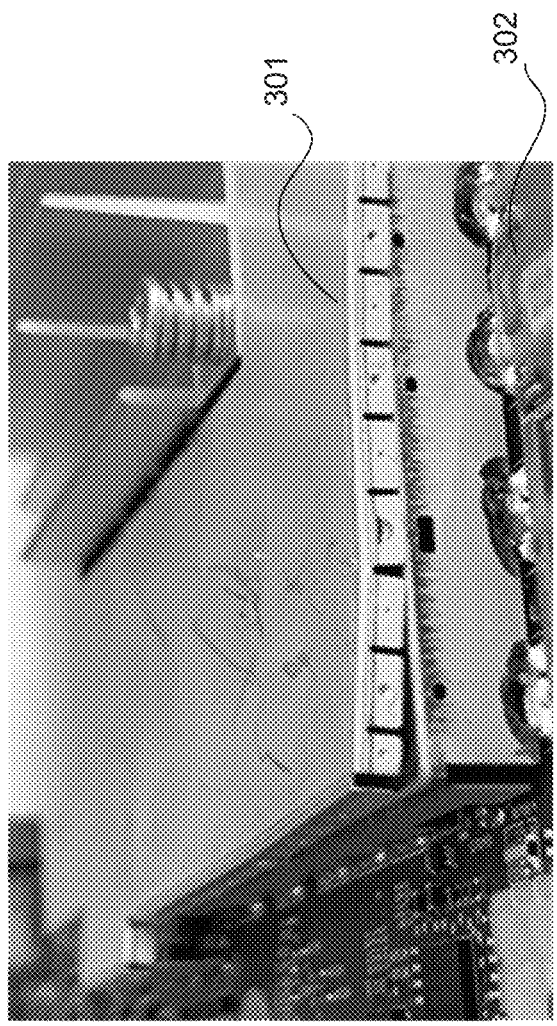
FIG. 3 is a view of an ultrasound system that includes a shield to cover sensitive electronics in the ultrasound system according to some embodiments.

FIG. 3 is a view 300 of an ultrasound system that includes a shield 301 that covers sensitive electronics, e.g., an oscillator, amplifier, IC, field programmable gate array (FPGA), and other sensitive electronics, in the ultrasound system according to some embodiments. However, whether during initial assembly or use of the ultrasound system (e.g., due to mechanical shock), the lid of shield 301 can lift from the body of shield 301, or the base of shield 301 may not make sufficient contact with a ground pad 302 on the PCB of the ultrasound system. Hence, EM emissions can leak from the ultrasound system.

As illustrated above in FIG. 2 and FIG. 3, the ultrasound system can include various grounding mechanisms to ensure proper grounding and prevent excessive EM emissions from leaking from the ultrasound system. In some embodiments, the indirect detector includes an electronic circuit to measure an impedance of a grounding mechanism in the ultrasound system. For example, the indirect detector can measure an impedance from the ground clip spring 201 to the grounding pad 202, an impedance from the shield lid of the shield 301 to a grounding pad 302, or other impedance that is indicative of the leak of the EM emissions.

An indirect detector can include any suitable electronic circuit to measure an impedance. In some embodiments, an indirect detector injects a current through a grounding mechanism, measures a voltage drop across the grounding mechanism, and determines the impedance as a ratio of the voltage drop to the injected current. In an embodiment, the indirect detector includes a current generator (e.g., current source) to generate the current as AC with a frequency corresponding to a frequency of EM emissions. For example, if an ultrasound system includes a 100 MHz oscillator, it is likely that EM emissions can occur at 100 MHz or a harmonic thereof. In at least some embodiments, the current generator generates an AC current at 100 MHz or a harmonic of 100 MHz for impedance measurement. The resulting impedance is generally complex-valued, and the impedance magnitude can be determined from the real and imaginary parts.

In some embodiments, an ultrasound system includes multiple grounding mechanisms for various circuits, and the circuits are associated with different frequencies. In some embodiments, the ultrasound system includes multiple indirect detectors, one for each of the circuits and each to generate AC current for impedance measurement at a frequency corresponding to the respective circuit. For example, an indirect detector for a 100 MHz oscillator can generate AC current at 100 MHz, and another indirect detector for an IC clocked at 80 MHz can generate AC current at 80 MHz. In some embodiments, the indirect detector uses a bridge method, such as, for example, an auto-balancing bridge method, or a resonant method to determine an impedance. The bridge methods are known to one of ordinary skill in the art.

Referring back to FIG. 1, detector 106 can include an indirect detector that compares a measured impedance to a threshold (e.g., 1-ohm or other impedance threshold, etc.). For a complex-valued impedance, the magnitude of the impedance can be compared to the threshold. If the impedance is greater than the threshold, then the indirect detector can configure a controller 105 to take an action, as described in further detail below. If the ultrasound system includes multiple indirect sensors for various circuits, the action can depend on which circuit fails the threshold comparison. In some embodiments, if a redundant circuit to the failed circuit is available, controller 105 disables the failed circuit and enables the redundant circuit. This disabling of the failed circuit and enabling of the redundant circuit can be done without changing a parameter of the ultrasound system, such as a power setting or imaging parameter. If a redundant circuit is not available, controller 105 can adjust a parameter of the ultrasound system to reduce the EM emissions caused by the circuit having the grounding mechanism with impedance above a threshold.

In some embodiments, controller 105 of the ultrasound system enables multiple indirect detectors in an order. For example, a direct detector can directly measure EM emissions having a spur at a certain frequency that is out of compliance. Controller 105 can then enable one or more indirect detectors (sequentially or simultaneously) based on the measurement from the direct detector. For example, controller 105 can look up in a table stored in a memory (not shown) for those circuits corresponding to the frequency of the spur, and enable indirect detectors for the circuits that correspond to the frequency to determine if grounding mechanisms for any of the circuits have impedance values above a threshold value. In some embodiments, the table can include a likelihood of EM emissions associated with each circuit, and controller 105 can sequentially enable the indirect detectors based on the likelihoods. For example, the table can associate an oscillator circuit with a high likelihood of EM emissions, an FPGA with a medium likelihood of EM emissions, and an analog-to-digital converter (ADC) with a low likelihood of EM emissions. In some embodiments, controller 105 can first enable an indirect detector for the oscillator circuit to determine if the grounding impedance is within threshold. If "yes" for the oscillator circuit, then controller 105 can enable an indirect detector for the FPGA to determine if it has a grounding mechanism with grounding impedance within threshold. If "yes" for the FPGA, then controller 105 can move to the ADC and enable its indirect detector to measure grounding impedance.

In some embodiments, an indirect detector includes a sensor, such as an accelerometer, that counts the number of times that a display monitor is opened and closed. If the count is greater than a threshold value, the indirect detector can send a signal to controller 105 to take an action, such as, for example, to notify the manufacturer or owner of the ultrasound system that a usage amount has been reached, or display a "service needed" icon. The count can represent an indication of failure, or reliability measure, since the ultrasound system is designed to be moved to a deployment location with the monitor in a closed position, and deployed for use at the location with the monitor in an open position. By opening and closing the monitor, shielding and/or cabling can fatigue and begin to leak EM emissions, and the threshold value used against the monitor open/close cycles can represent a number of cycles at which the shielding and/or cabling is expected to fatigue and begin leaking the EM emissions.

In some embodiments, the detector can include an indirect detector that determines an amount of EM emissions, a type of EM emissions, or both the amount and type of EM emissions based on an ultrasound image generated by the ultrasound system. In some embodiments, the indirect detector includes a neural network.

Figure 4A:
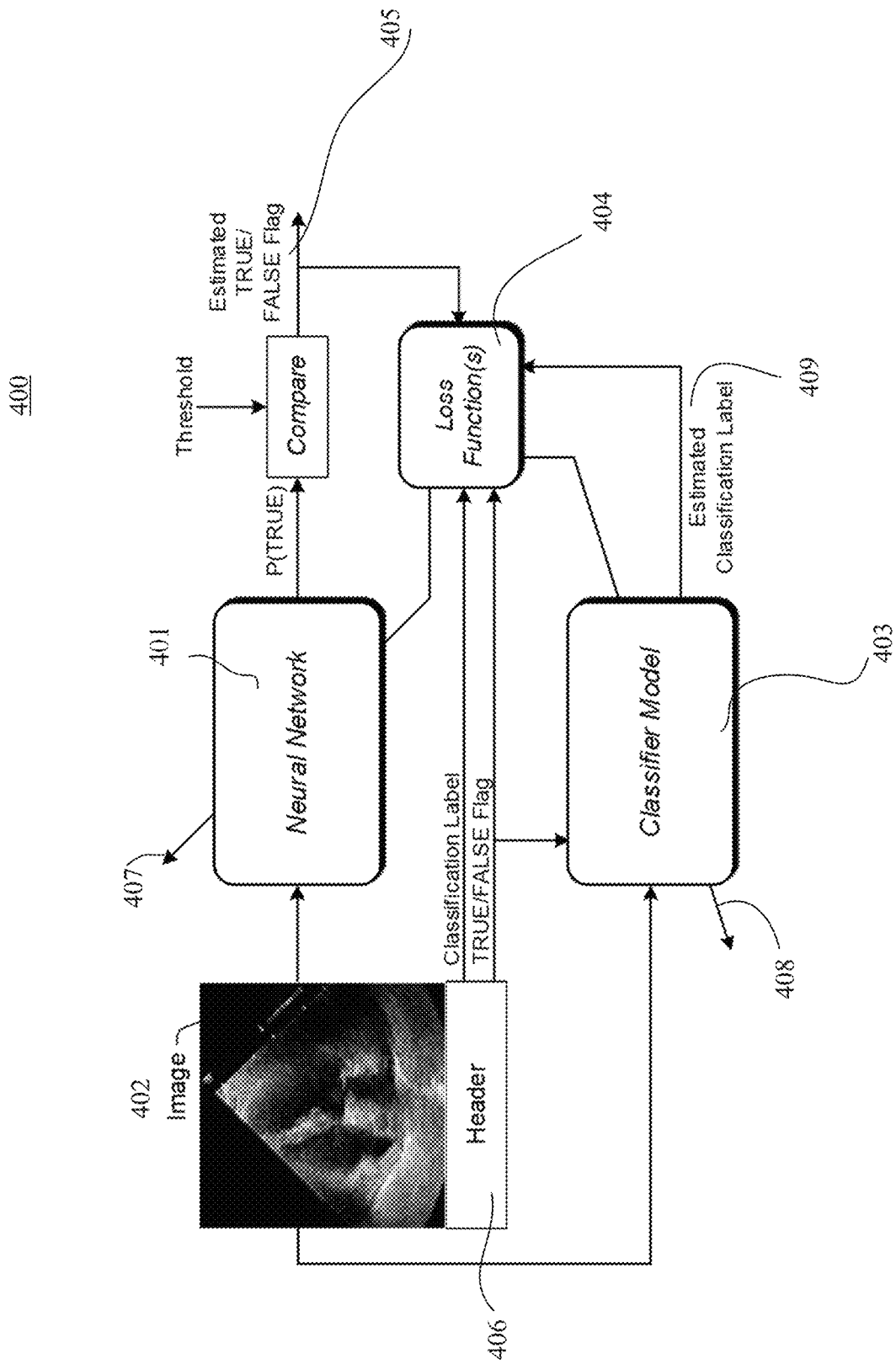
FIG. 4A is a view illustrating an indirect detector to detect EM emissions according to some embodiments.

FIG. 4A is a view 400 illustrating an indirect detector to detect EM emissions according to some embodiments. The indirect detector includes a neural network 401 to detect presence of EM emissions and a classifier model 403 to determine a classification of EM emissions. In some embodiments, classifier model 403 identifies a region of interest (ROI) in the ultrasound image associated with the classification. In some embodiments, the indirect detector includes one or more processors coupled to the neural network and the classifier model to perform methods to detect EM emissions as described herein. Neural network 401 is trained with ultrasound images corrupted from EM emissions and labeled with a TRUE flag and with additional ultrasound images that are not corrupted from EM emissions and that are labeled with a FALSE flag (e.g., ground truth training images).

As shown in FIG. 4A, an ultrasound image 402 is an example of a ground truth training image and is supplied to neural network 401 and classifier model 403. In some embodiments, a true/false flag is included in a header 406 of ultrasound image 402. In some embodiments, a classification label is included in the header of ultrasound image 402. In some embodiments, neural network 401 generates a probability P(TRUE) that ultrasound image 402 processed by the neural network is corrupted by EM emissions. The probability P(TRUE) is compared to a threshold value and a binary indicator 405 (e.g., estimated TRUE/FALSE flag) that indicates whether or not the ultrasound image is corrupted by EM emissions is generated based on results of the comparison. For example, if the probability P(TRUE) is greater than the threshold value, then the binary indicator 405 can indicate a TRUE condition (e.g., the ultrasound image is corrupted by EM emissions). During training, coefficients of the neural network are adjusted based on comparing binary indicator 405 to the TRUE/FALSE flag of the ground truth training images using one or more loss functions 404. Generally, the loss function in a neural network quantifies a difference between an expected outcome and the outcome produced by the machine learning model to adjust the coefficients of the neural network. During deployment, binary indicator 405 generated by a trained neural network can be provided to the controller, which can take an action when the binary indicator indicates that one or more ultrasound images are corrupted by EM emissions.

As shown in FIG. 4A, neural network 401 is separate from classifier model 403. In some other embodiments, neural network 401 includes the classifier model 403. In some embodiments, classifier model 403 is trained to generate a classification label corresponding to a type of EM emissions that can corrupt an ultrasound image. Examples of classification labels include, but are not limited to, "spurious" for narrowband EM emissions, "harmonic" for EM emissions having a fundamental tone and one or more harmonics or sub-harmonics, "broadband" for EM emissions having a bandwidth greater than a threshold bandwidth, "burst" for time-gated EM emissions, and any suitable statistical classification label corresponding to EM emissions fitting a known random process (e.g., Gaussian, Rayleigh, or other random process). During deployment, a classification label 409 generated by a classifier model 403 can be provided to the controller, which can take an action based on the type of EM emissions indicated by the classification label.

As shown in FIG. 4A, during training, one or more error terms 407 can be generated by the loss function 404 and provided to neural network 401 to adjust coefficients of the neural network 401. One or more error terms 408 can be generated during training by the loss function 404 and provided to classifier model 403 to adjust coefficients of the classifier model 403.

For example, true classification labels can be added to the labels of the ground truth training images (e.g., by experts). The true classification labels can be provided to one or more loss functions 404 that generates the error terms 408 based on the true classification labels and the estimated classification label 409 to train the classifier model 403. In some embodiments, classifier model 403 is trained to indicate positions on the ultrasound image with artifacts of EM emissions.

As shown in FIG. 4A, a TRUE/FALSE flag from the ground truth training image is supplied to classifier model 403, so that classifier model 403 can be updated only for training images corrupted by EM emissions (e.g., when the flag is TRUE). In some embodiments, the TRUE/FALSE flag from the ground truth training image that is supplied to classifier model 403 is replaced with the estimated TRUE/FALSE flag generated by neural network 401. In this case, classifier model 403 and neural network 401 can be jointly trained by adjusting one or more coefficients of the classifier model 403 only for training images for which the neural network 401 generates the estimated TRUE/FALSE flag as TRUE.

Figure 4B:
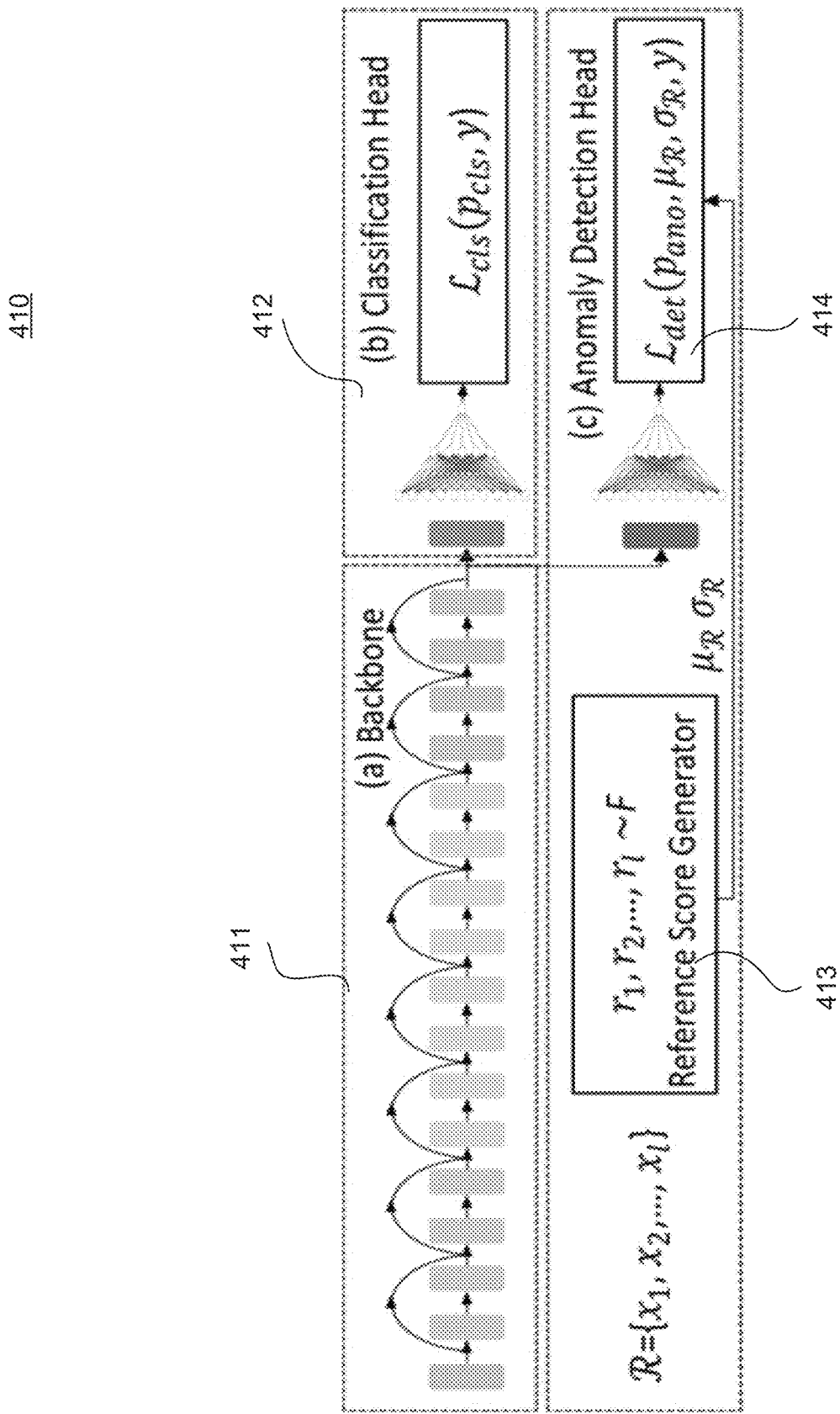
FIG. 4B is a diagram showing a neural network to detect EM emissions from ultrasound images according to some embodiments.

FIG. 4B is a diagram 410 showing a neural network to detect EM emissions from ultrasound images according to some embodiments. Referring to FIG. 4B, the neural network includes one or more processors coupled to a common backbone module 411 that is connected to both a classification head module 412 and an anomaly detection head module 414. In some embodiments, the processor coupled to common backbone module 411 extracts features from one or more ultrasound images that are input to common backbone module 411. Processor provides the extracted features to the classification head module 412 that classifies, using the processor, the input images based on the extracted features. As shown in FIG. 4B, anomaly detection head 414 receives the extracted features and detects, using a processor, an anomaly (e.g., a noise process, such as an EM emissions, or other noise) in the one or more ultrasound images that are input to backbone module 411. In FIG. 4B, the anomaly detection head module 414 detects, using a processor, an anomaly based on reference scores μR, σR that are generated by a reference score generator module 413 and assigned to the one or more input ultrasound images. In some embodiments, the neural network that detects EM emissions on ultrasound systems is a convolutional neural network.

Embodiments of a Controller

The controller (e.g., controller 105 in FIG. 1) can take one or more actions in response to receiving a signal from one or more detectors, including one or more of electrical actions, mechanical actions, and enabling notifications. The electrical actions can be, for example: reducing a power of a circuit (e.g., amplifier gain, voltage swing, current swing, etc.); enabling a redundant circuit and disabling the "problem" circuit; changing an operating frequency (e.g., transducer frequency, system/clock frequency of FPGA/IC, etc.); changing an order of events (e.g., order of enabling transducer elements, enable an interleaver or scrambler, etc.); enabling a calibration routine (e.g., reconfigure a digital filter's notch level or cutoff frequency, redistribute gain throughout an amplifier chain, etc., to match a target parameter, such as, for example, signal-to-noise ratio (SNR)); change a mode (e.g., enter a "limp mode", enable an alternative mode to a known "corner case" mode, determine an amount of margin and enable a higher-performing mode than the current mode based on the margin, etc.), as described in further detail below.

The mechanical actions can include, for example, enabling a hardware element (e.g., cam, actuator, etc.) to adjust a grounding mechanism (tighten screw, clamp, spring, etc.) and thus reduce EM emissions. Enabling notifications can include, for example, notifying a service technician to repair the ultrasound system, notifying the manufacturer (including suitable data, such as configuration of the ultrasound system, model and serial number, operator description, e.g., name, title, employer, etc.), and notifying an owner or a department head. In some embodiments, notifications are enabled in a user interface on a display device of the ultrasound machine. In some embodiments, the notifications include at least one of a "check engine light" icon, a request for a user approval to take an action (e.g., before changing an imaging mode), a list of options to reduce EM emissions, a warning with a description of consequences if changes are not made (e.g., risk to a patient, risk of affecting another medical device, a message to expect interference in an ultrasound image, etc.), and an indication of a region in the ultrasound image to expect artifacts.

The signal provided to the controller from a detector can include any suitable indicator, such as an indicator that EM emissions are present, an indicator of an amount of EM emissions, an indicator of a type of EM emissions, an indicator of a poor ground, a TRUE/FALSE flag, a classification label, or other indicator. In some embodiments, the controller takes an action to affect an electrical circuit and/or a parameter of the ultrasound system. For example, the controller can reduce the power of a circuit associated with a signal provided by one or more detectors, such as a circuit for which a poor ground has been identified (e.g., due to a high impedance measurement) or a circuit associated with a frequency of detected EM emissions (e.g., an oscillator that generates a 100 MHz tone or amplifier that amplifies a 100 MHz tone when EM emissions are detected having a 100 MHz component) to reduce the amount of EM emissions generated by the ultrasound system. Reducing the power of a circuit can include reducing the gain of an amplifier, reducing the voltage swing of a signal, reducing the current swing of a signal, etc.

In some embodiments, the ultrasound system includes one or more redundant circuits, and in response to receiving a signal from a detector, the controller disables a circuit associated with EM emissions and enables a redundant circuit to the circuit. In some embodiments, the ultrasound system includes multiple integrated circuits (ICs) that are redundant to one another, such as multiple ICs with oscillators and amplifier chains, and each of the ICs is covered by its own shield to limit the EM emissions radiated by the IC. When a detector determines that the magnitude of an impedance from the shield of one IC to a ground pad of a PCB on which the IC is mounted is greater than a threshold value, the detector can send a signal to the controller. In response to receiving the signal from the detector, the controller can disable the IC and enable another IC that is redundant to the IC.

In some embodiments, the controller changes a frequency of the ultrasound system responsive to receiving a signal from one or more detectors. For example, the controller can change an operating frequency of a transducer of a scanner to reduce EM emissions and/or change a frequency component of EM emissions. In some embodiments, the controller changes a system frequency (e.g., clock frequency) of a subsystem, IC, FPGA, etc. of an ultrasound system. For example, an FPGA can operate based on one of many clock frequencies (e.g., a range of clock frequencies), and the controller can change the clock frequency from one end of the range to another end of the range to reduce or alter the EM emissions.

In some embodiments, the controller changes an order of events in response to receiving a signal from one or more detectors. For example, the controller can change the order in which the transducer elements of a scanner are enabled. The order in which the transducer elements are enabled can be changed according to frequency (e.g., transducer elements for a higher frequency array can be enabled prior to transducer elements of a lower frequency array in a multi-frequency array). In some embodiments, the order can change the transducer elements in a multi-dimensional array by enabling transducer elements at first positions before or after transducer elements at second positions (e.g., left, right, different rows, etc.). Changing the order in which the transducer elements are enabled can include adding a delay or removing a delay to an activation signal provided to one or more of the transducer elements.

In some embodiments, changing an order of events includes enabling an interleaver circuit that interleaves one or more signals with each other (e.g., alternates from one signal to another and then another, and repeats this alternating to generate an interleaved signal). In some embodiments, changing an order of events includes enabling a scrambler that receives an input signal and generates a scrambled signal based on the samples of the input signal and a scrambling sequence. By scrambling the samples of the input sample, the generated scrambled signal can reduce the undesired effects, such as distortions, of EM emissions to the input signal by decorrelating noise across samples of the input signal, which can result in a higher quality ultrasound image. The order of samples of the scrambled signal can be recovered (e.g., de-scrambled) to match the order of samples of the input signal based on the scrambling sequence.

In some embodiments, the controller enables the execution of a calibration routine on the ultrasound system in response to receiving a signal from one or more detectors. The calibration routine can be based on a property of the EM emissions determined by a detector, such as a frequency component and an amplitude of the frequency component, and calibrate a circuit based on the property. For example, the calibration routine can reconfigure a digital filter according to the property, e.g., by changing a cutoff frequency of the filter, changing a notch depth of the filter (e.g., by adding another pole), changing the dampening of a filter response, reconfiguring the structure of the filter (e.g., changing a transversal filter to an infinite impulse response filter), and the like.

In some embodiments, the calibration routine redistributes power within an amplifier chain, e.g., by setting the gain of a first amplifier from a first gain to a second gain, and setting the gain of a second amplifier from a third gain to a fourth gain. By redistributing amplifier gains, harmonic components that can contribute to EM emissions can be reduced.

In some embodiments, the controller takes an action to change a mode of the ultrasound system. For example, the controller can enable a "limp mode" of the ultrasound system, in which performance of the ultrasound system can be reduced to also reduce EM emissions. As an example, the limp mode can reduce the power of ultrasound generated by a scanner of the ultrasound system, which can reduce the image quality of ultrasound images generated by the ultrasound system. In at least some embodiments, a limp mode reduces an amount of data in an ultrasound image, such as a number of pixels, a number of channels used to generate the ultrasound image, etc.

In some embodiments, the controller takes an action to change an imaging mode of the ultrasound system. An imaging mode of the ultrasound machine can be, for example, a 2-dimensional (2-D) or brightness mode (B-mode), motion mode (M-mode), a Doppler mode (spectral, color flow, and power), or other imaging mode. For example, some imaging modes may be known to be "corner cases" for EM emissions by causing higher EM emissions than other imaging modes. The controller can store or have access to a mapping of imaging modes to EM emissions and their properties, such as types of EM emissions caused by the imaging mode, frequency components of EM emissions caused by the imaging mode, etc. The mapping can also include alternative imaging modes to each imaging mode. Based on a property of the EM emissions determined by a detector and a current imaging mode, the controller can select an alternative imaging mode based on the mapping and enable the alternative imaging mode to thereby reduce EM emissions.

In some embodiments, the controller takes an action to change a mode of the ultrasound system from a first mode to a second mode based on one or more signals received from a detector regarding EM emissions, where the second mode has better performance than the first mode. For example, the signal from the detector can indicate one or more properties related to the EM emissions, and the controller can determine that an amount of margin exists based on the one or more properties. As an example, the controller can compare frequency properties of the EM emissions to an allowable spectral mask and, based on the comparison, determine an amount of available margin. Based on this margin, the controller can determine an alternative imaging mode to enable that can increase performance of the ultrasound system (e.g., improve image quality) while still maintaining EM emissions below the spectral mask. Hence, based on the detected EM emissions, the ultrasound system can reconfigure itself to improve imaging performance.

In some embodiments, the controller takes an action to affect a mechanical change. For example, the ultrasound system can include any suitable mechanical device (e.g., as a part of the controller) that can be coupled to a hardware element intended for grounding, such as the ground spring clip 201 in FIG. 2 and the shield 301 in FIG. 3. The mechanical device can include a mechanism to tighten the hardware element, including to close a gap between the hardware element and a ground pad, or generally to improve the grounding. For example, the mechanical device can include a spring, screw, cam, clamp, etc., and an actuator for the mechanical device, such as a motor. The controller can enable the actuator to adjust the mechanical device, such as to tighten a spring or screw, rotate a cam, close a clamp, etc., to improve the grounding by reducing the impedance from the hardware element to a ground pad. In this way, the ultrasound system can be self-correcting and improve grounding to reduce EM emissions.

In some embodiments, the controller sends or causes to be sent a notification based on receiving a signal from one or more detectors. For example, the controller can send a notification to a service technician with a request to repair the ultrasound system and bring the EM emissions into compliance. In some embodiments, the controller can send a notification to the manufacturer of the ultrasound system. The notification can include any suitable data regarding the EM emissions or operation of the ultrasound system, such as data from one or more sensors. The data can include data regarding the ultrasound system, such as a configuration of the ultrasound system when EM emissions are detected, a description of an operator of the ultrasound system, including a name, title, employer, etc., a model and serial number of the ultrasound system, and the like. In some embodiments, the controller sends a notification to an owner of the ultrasound system, such as, for example, a hospital employee. In some embodiments, the controller can send a notification to an employee of a care facility that operates the ultrasound system, such as, for example, a department head or administrator for a department associated with the ultrasound system (e.g., an ultrasound system assigned to an Emergency Department of a hospital).

In some embodiments, the controller can take an action to affect a user interface of the ultrasound system. For example, the controller can determine an action to take based on a signal from a detector, and before taking the action, the controller can display on the user interface a request for user approval. The user interface can display a message that describes a recommendation to change an imaging mode based on detected EM emissions, and an option for user selection to enable the change of imaging mode. The user's approval may be required to affect the change. In some embodiments, the controller causes the user interface to display a list of available options to enable based on EM emissions, such as a list of imaging modes available from the mapping described above based on the current imaging mode and information from a signal provided by a detector. In an embodiment, the list of imaging modes includes at least one imaging mode that improves the image quality compared to the current imaging mode, as described above.

In at least some embodiments, the controller causes the user interface to display a warning based on a signal provided from a detector regarding EM emissions. The warning can include a description of consequences if changes are not made, such as a risk to a patient, risk of affecting another medical device, a message to expect interference in an ultrasound image as a result of EM emissions, etc. The warning can include a list of equipment in proximity to the ultrasound system (e.g., within the same room as the ultrasound system) that could be affected by EM emissions from the ultrasound system. The warnings can be tiered according to severity, with a number of tiers, such as three. A first tier can represent little risk or concern (e.g., EM emissions may be higher than usual, but still compliant with guidelines). A second tier can represent a medium risk or concern (e.g., EM emissions are non-compliant but still less than a level that would affect another medical device in proximity to the ultrasound system), and a third tier can represent significant risk or concern (e.g., EM emissions are of a type to affect a medical implant on a patient). In some embodiments, the user interface displays an icon, such as a "check engine light icon" to indicate a warning. The icon can be changed to indicate a tier (or level) of the warning, such as a constant green for the first tier, a constant red for the second tier, and a blinking red for the third tier.

In some embodiments, the controller causes the user interface to indicate a region on an ultrasound image that could be (or is likely to be) affected by EM emissions, such as by having artifacts caused by EM emissions. For example, a detector may include a neural network and classifier as described above, and the neural network or classifier can be trained to indicate positions on the ultrasound image with artifacts of EM emissions. Based on this information, the user interface can display a region indicator on the ultrasound image and a warning to expect interference in the region.

In some embodiments, the controller determines that, based on properties of the EM emissions, a certain region or property of the ultrasound image is likely to be affected. For example, EM emissions having frequency components in a first range may be associated with distortion in a certain region of an ultrasound image when a particular imaging mode is used, due to the frequency components interfering with the frequency of ultrasound used in the imaging mode. The far field objects (e.g., deeper objects) can be more likely to be affected by EM emissions than near field objects (e.g., shallower objects). In some embodiments, the user interface displays a bounding box around far field objects and/or a warning that distortion may be present in the far field. In some embodiments, EM emissions of a first type (e.g., of a first classification label) are associated with a first type of interference, such as pixelization or a herringbone pattern, and EM emissions of a second type (e.g., of a second classification label) are associated with a second type of interference, such as compression along an axis. In some embodiments, the controller causes the user interface to display a warning indicating what type of interference to expect in an ultrasound image based on a classification label provided to the controller by a detector.

The ultrasound systems disclosed herein provide numerous advantages over conventional ultrasound systems that do not detect EM emissions. The ultrasound systems disclosed herein can provide self-correction of a circuit that is leaking EM emissions, such as by disabling it and enabling a redundant circuit, mechanically adjusting a shield over the circuit, or changing a parameter of the circuit. The ultrasound systems disclosed herein can guarantee that EM emissions generated throughout the life of the ultrasound system remain in compliance with regulatory guidelines that is better than an existing approach of emulated environmental testing and statistical inference. Rather than being sent out for repair, the ultrasound system disclosed herein can remain deployed and available for use, thus improving patient care. The ultrasound systems disclosed herein can reduce the impact on proximate medical devices and possible harm to a patient, and maintain a positive brand image for the manufacturer, as described in further detail below.

For example, the ultrasound systems described herein can detect when EM emissions are not compliant with EM emission guidelines and display a warning to the operator of the ultrasound system, such as a warning that a nearby medical device could be affected. Hence, rather than affecting another medical device and possibly harming a patient, the operator may make a change to correct the EM emissions, such as by running a calibration routine to recalibrate the ultrasound system. In some embodiments, the ultrasound systems can self-correct a circuit that is leaking EM emissions, such as by disabling it and enabling a redundant circuit, mechanically adjusting a shield over the circuit, or changing a parameter of the circuit to affect the EM emissions. Hence, the ultrasound system can guarantee that EM emissions generated throughout the life of the ultrasound system remain in compliance with regulatory guidelines. Moreover, the ultrasound system does not need to be sent out for repair, and instead can remain deployed and available for use, thus improving patient care. This is especially true in care locations with limited numbers of ultrasound machines. In some embodiments, a calibration routine alters one or more circuits so that a signal parameter of the ultrasound system matches a calibration level. For example, a current source can be adjusted so that a signal to noise ratio (SNR) measurement within the ultrasound system matches a target SNR.

Figure 5:
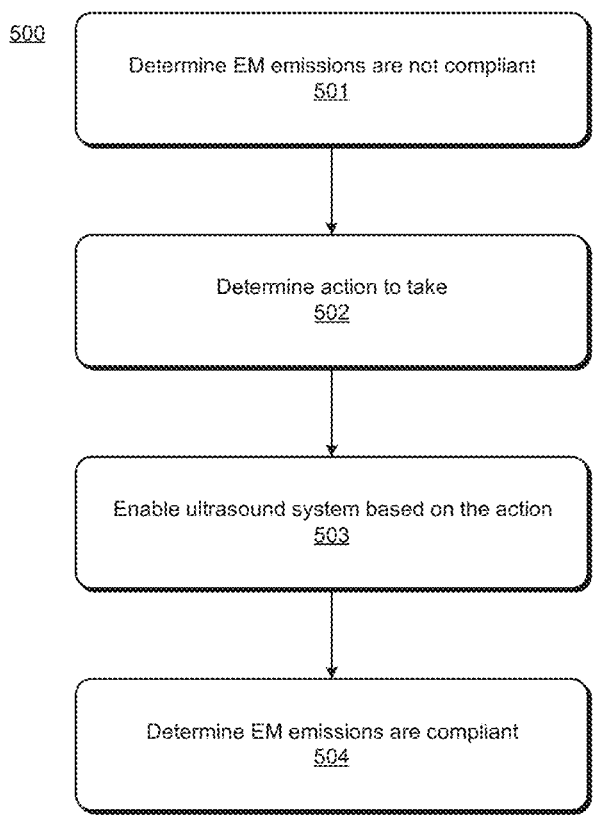
FIG. 5 is a flowchart of a method for an ultrasound system to autonomously detect and correct EM emissions according to some embodiments.

FIG. 5 is a data flow diagram of a process 500 for an ultrasound system to autonomously detect and correct EM emissions according to some embodiments. The process is performed by processing logic that may comprise hardware (circuitry, dedicated logic, etc.), software (such as is run on a general-purpose computer system or a dedicated machine), firmware, or a combination thereof. In some embodiments, the ultrasound system includes one or more processors and a memory coupled to the processor(s) to perform the process.

Process 500 begins by processing logic determining that EM emissions are not compliant to the ultrasound system guidelines at block 501. In some embodiments, the guidelines for the ultrasound system are stored in the memory of the ultrasound system. Process 500 continues at block 502 where processing logic determines an action that needs to be taken to correct the detected EM emissions. At block 503, processing logic enables the ultrasound system based on the determined action. After performing the action to correct the EM emissions, processing logic determines that the EM emissions are compliant to the ultrasound system guidelines at block 504, as described above.

Figure 6:
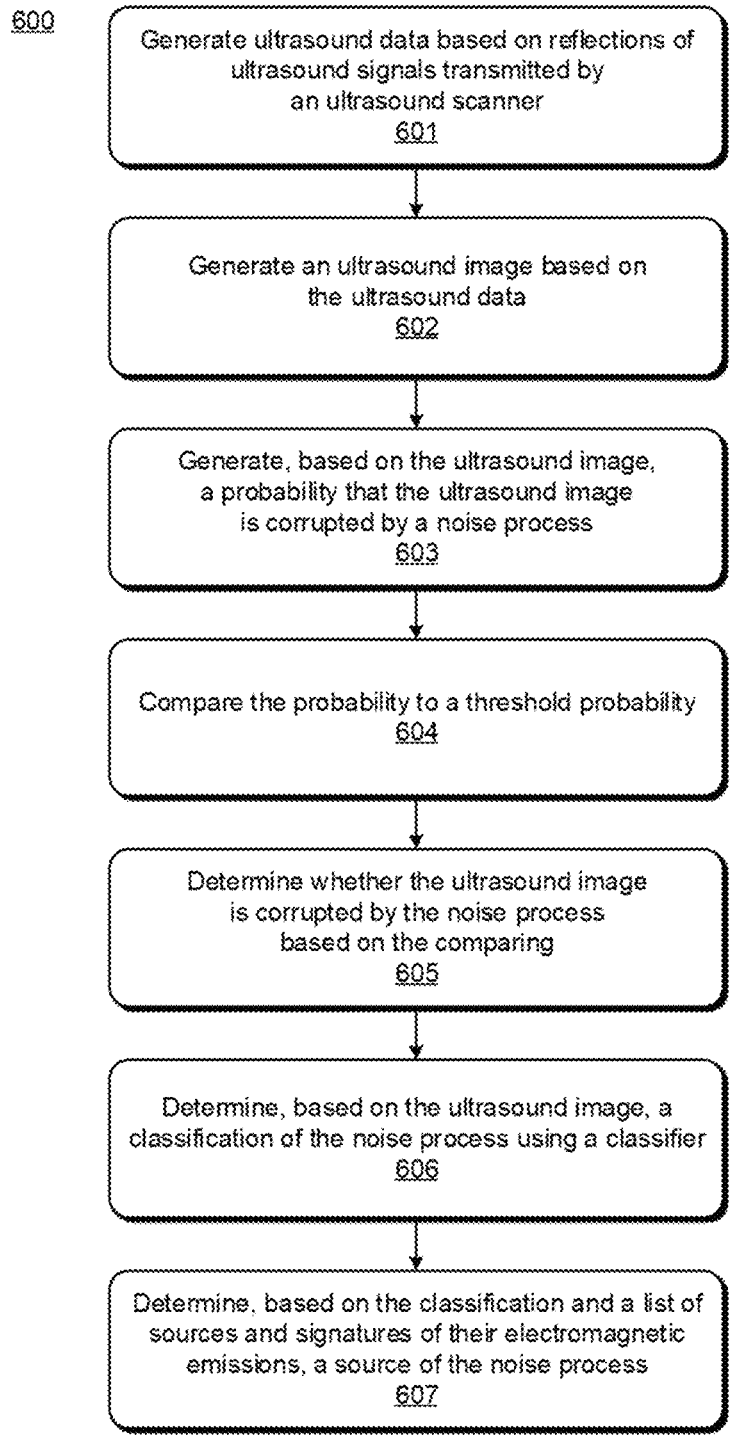
FIG. 6 is a data flow diagram of a process for an ultrasound system to detect a noise process according to some embodiments.

FIG. 6 is a data flow diagram of a process 600 for an ultrasound system to detect a noise process according to some embodiments. The process is performed by processing logic that may comprise hardware (circuitry, dedicated logic, etc.), software (such as is run on a general-purpose computer system or a dedicated machine), firmware, or a combination thereof. In some embodiments, the ultrasound system includes one or more processors to perform the process.

Referring to FIG. 6, the process 600 starts at block 601 with processing logic generating ultrasound data based on reflections of ultrasound signals transmitted by an ultrasound scanner, as described above. At block 602, processing logic generates an ultrasound image based on the ultrasound data, as described above. At block 603, processing logic determines a probability that the ultrasound image is corrupted by a noise process. This determination can be made by a circuit coupled to the ultrasound machine, as described above.

In some embodiments, the noise process includes electromagnetic emissions, and the circuit is implemented by the ultrasound machine and includes a neural network, as described above. At block 604, processing logic compares the probability that the ultrasound image is corrupted by a noise process to a threshold probability. The comparison can be performed using one or more processors coupled to the neural networks, as described above. At block 605, processing logic determines, based on the comparing, whether or not the ultrasound image is corrupted by the noise process, as described above. In some embodiments, the ultrasound machine generates the ultrasound image as part of an ultrasound examination administered with the ultrasound system, and the circuit makes the determination as to whether the ultrasound image is corrupted by the noise process during the ultrasound examination. In some embodiments, the ultrasound system includes a classifier. In some embodiments, the classifier is coupled to the processor. At block 606, processing logic determines a classification of the noise process using a classifier model, as described above. At block 607, processing logic determines a source of the noise process based on the classification and a list of sources and signatures of their electromagnetic emissions, as described above.

Figure 7:
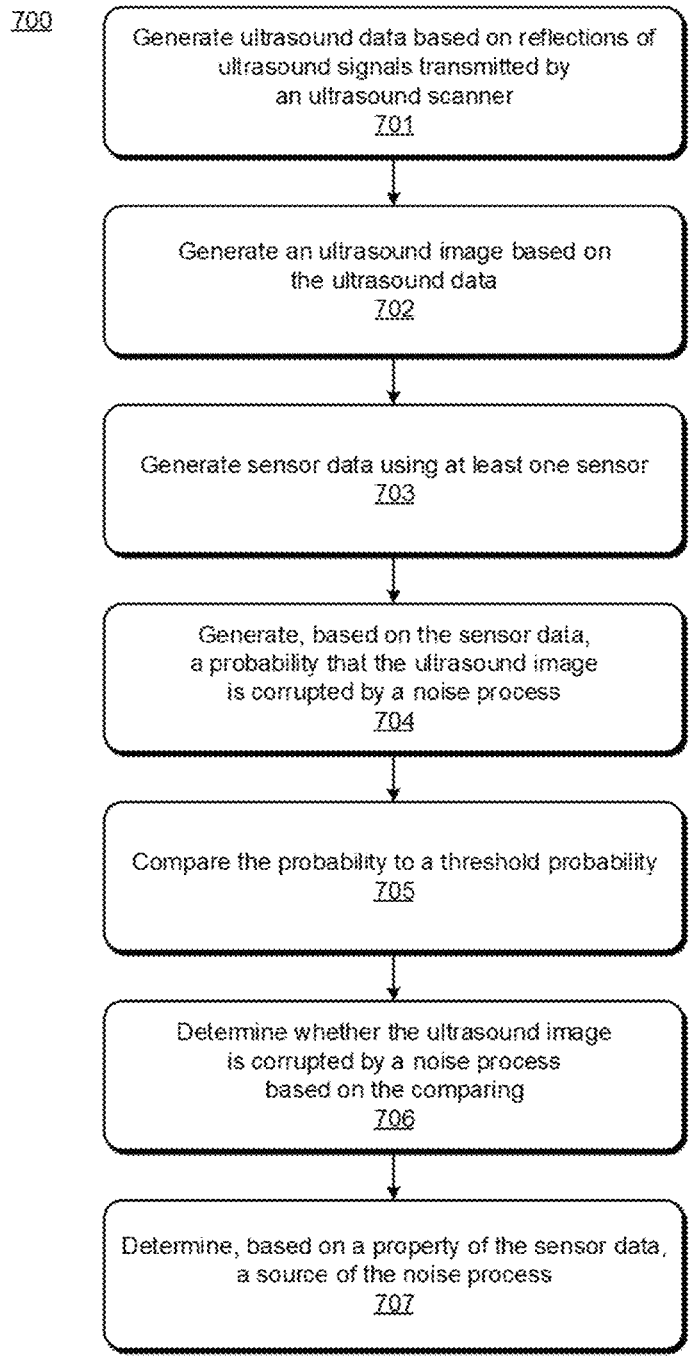
FIG. 7 is a data flow diagram of a process for an ultrasound system to detect a noise process according to some other embodiments.

FIG. 7 is a data flow diagram of a process 700 for an ultrasound system to detect a noise process according to another embodiment. The process is performed by processing logic that may comprise hardware (circuitry, dedicated logic, etc.), software (such as is run on a general-purpose computer system or a dedicated machine), firmware, or a combination thereof. In at least some embodiments, the ultrasound system includes one or more processors and at least one sensor coupled to the processor(s).

Referring to FIG. 7, the process 700 starts at block 701 with processing logic generating ultrasound data based on reflections of ultrasound signals transmitted by an ultrasound scanner, as described above. At block 702, processing logic generates an ultrasound image based on the ultrasound data, as described above. At block 703, processing logic generates sensor data, as described above. The processing logic can be part of one or more sensors.

At block 704, processing logic generates a probability that the ultrasound image is corrupted by a noise process. This determination can be made by a circuit coupled to the ultrasound machine, based on the sensor data, as described above. In some embodiments, at least one sensor includes an impedance sensor, and the sensor data includes an impedance. In some embodiments, the impedance sensor includes a current source to generate a current at a non-zero frequency selected based on frequency content of electromagnetic emissions, and the impedance is complex-valued, as described above. In some embodiments, the impedance sensor generates the impedance from a first point to a ground point of the ultrasound system, the first point including at least one of a position on a ground spring clip and a position on a shield, as described above. In some embodiments, the at least one sensor includes impedance sensors located within the ultrasound machine and generates, using the processor, an impedance matrix including impedances between the impedance sensors. In some embodiments, the determination of impedance is performed by a circuit coupled to the processor, whether the ultrasound image is corrupted by a noise process based on the impedance matrix. In some embodiments, the circuit is part of the ultrasound machine and includes a neural network, as described above. In some embodiments, processing logic generates a probability that the ultrasound image is corrupted by the noise process. The generation of the probability can be performed by one or more processors coupled to the neural networks, based on the impedance matrix. In an example, a neural network generates the probability by processing the impedance matrix.

At block 705, processing logic compares the probability that the ultrasound image is corrupted by the noise process to a threshold probability. This comparison may be made by one or more processors coupled to the neural networks, as described above. At block 706, processing logic determines whether the ultrasound image is corrupted by the noise process based on the comparison. In some embodiments, the noise process includes EM emissions and the sensor data is indicative of the EM emissions.

At block 707 processing logic determines a source of the noise process based on a property of the sensor data. In some embodiments, the source of EM emissions is determined by correlating the property of the sensor data with properties known to be associated with the EM emissions that are stored in a memory. In some embodiments, the property of the sensor data includes at least one of a frequency content and a statistical classification. In some embodiments, the sensor data includes a number of open/close cycles of a display monitor device of the ultrasound machine.

In some embodiments, at least one sensor includes a light sensor, and the sensor data includes an amount of light. For example, the detector can compare the amount of light sensed by the light sensor in a proximity of a shield (e.g., a Faraday cage, or other shield) that covers sensitive electronics in the ultrasound machine with a predetermined threshold that indicates that there is a likely opening in the shield through which EM emissions are escaped. If the amount of light sensed by the light sensor is greater than the predetermined threshold, the light sensor generates a signal to the controller to take a corrective action to reduce EM emissions. In an example, the light sensor is included inside a shield that covers electronics. If there is an opening in the shield, the light sensor can detect light.

FIG. 8 is a data flow diagram of a process 800 for an ultrasound system to detect electromagnetic emissions according to some embodiments. The process can be performed by processing logic that may comprise hardware (circuitry, dedicated logic, etc.), software (such as is run on a general-purpose computer system or a dedicated machine), firmware, or a combination thereof. In at least some embodiments, the ultrasound system includes one or more processors and at least one sensor coupled to the processor(s) to perform the process. Additionally or alternatively, the ultrasound system includes one or more processors to perform the process.

Referring to FIG. 8, the process 800 starts at block 801 with processing logic, e.g., processing logic of at least one direct and/or indirect sensor, implemented to generate sensor data indicative of an operating environment within an ultrasound machine. The sensor data can include impedance measurements, RF measurements, ADC samples, an amount of light, a number of monitor open/close cycles, and the like, as described above. At block 802, processing logic generates, based on the sensor data, a report of electromagnetic emissions within the operating environment. The report can include the sensor data and any data related to, or derived from, the sensor data. In an embodiment, the report indicates a spectral content of the electromagnetic emissions. Additionally or alternatively, the report can indicate an amount of available margin of the electromagnetic emissions relative to a spectral mask based on the spectral content of the electromagnetic emissions. In some embodiments, content of the report is included in a notification sent by a controller, such as the controller 105 in FIG. 1. Accordingly, the processing logic can display content of the report on a user interface of the ultrasound machine, send content of the report to a manufacturer of the ultrasound machine, include content of the report in a notification sent to a repair technician, and the like, as described above.

In an embodiment, the report includes a probability of the electromagnetic emissions within the operating environment, and at least one sensor includes impedance sensors located within the ultrasound machine that is configured to generate an impedance matrix including impedances between the impedance sensors as the sensor data. The processing logic can be implemented to generate the probability based on the impedance matrix. For instance, a neural network can process the impedance matrix and generate a probability that electromagnetic emissions exist within the operating environment of the ultrasound machine.

At block 803, processing logic determines, based on the sensor data, a classification of the electromagnetic emissions. For example, the processing logic can be implemented as a classifier model, such as classifier model 403 in FIG. 4, to generate a classification of the electromagnetic emissions. The classification can include an estimated classification label, as described above. At block 804, processing logic determines, based on the classification, a source circuit of the electromagnetic emissions within the ultrasound machine. For instance, the processing logic can address a listing/mapping of source circuits and their electromagnetic signatures, including EM classifications, to determine the source circuit responsible for the electromagnetic emissions within the ultrasound machine. The ultrasound machine can store the listing/mapping, and/or obtain the listing/mapping from an additional device, such as a server device in a care facility.

At block 805, processing logic disables the source circuit, and at block 806, processing logic enables an additional source circuit that is redundant to the source circuit. For instance, the source circuit can include a first oscillator that is responsible for leaking the EM emissions, and the additional source circuit can include a second oscillator that is redundant to the first oscillator, e.g., it can function in a similar or same fashion as the first oscillator, albeit without leaking EM emissions. Hence, the ultrasound machine can self-correct itself when it determines it has EM emissions.

It is apparent from this description that embodiments and aspects of the present invention may be embodied, at least in part, in software. That is, the techniques and methods may be carried out in a data processing system or set of data processing systems in response to one or more processors executing a sequence of instructions stored in a storage medium, such as a non-transitory machine readable storage media, such as volatile dynamic random access memory (DRAM) or nonvolatile flash memory. In various embodiments, hardwired circuitry may be used in combination with software instructions to implement the embodiments described herein. Thus, the techniques and methods disclosed herein are not limited to any specific combination of hardware circuitry and software, or to any particular source for the instructions executed by the one or more data processing systems.

In the foregoing specification, specific exemplary embodiments have been described. It will be evident that various modifications may be made to those embodiments without departing from the broader spirit and scope set forth in the following claims. The specification and drawings are, accordingly, to be regarded in an illustrative sense rather than a restrictive sense.

In the foregoing specification, EM emissions are described as an example noise process. However, one skilled in the art would recognize that the methods, devices, and systems disclosed herein can be used to detect and/or correct for any suitable type of noise process, including electrostatic noise, noise due to microphonics, thermal noise, intermodulation noise, and the like.

What is claimed is:
1. An ultrasound system comprising:
    an ultrasound scanner configured to generate ultrasound data based on reflections of ultrasound signals transmitted by the ultrasound scanner;

an ultrasound machine configured to generate ultrasound images including a first ultrasound image and a second ultrasound image based on the ultrasound data; and a circuit configured to make a determination whether the first ultrasound image is corrupted by a noise process that includes electromagnetic emissions of a plurality of types including a first type and a second type; wherein the circuit includes a neural network and a classifier coupled to the neural network and configured to determine the electromagnetic emission as of the first type based on the first ultrasound image and the electromagnetic emissions as of the second type based on the second ultrasound image.

2. The ultrasound system as described in claim 1, wherein the circuit is implemented by the ultrasound machine and the neural network is configured to:

generate, based on the first ultrasound image, a probability that the first ultrasound image is corrupted by the electromagnetic emissions; and compare the probability to a threshold probability to make the determination.

3. The ultrasound system as described in claim 1, wherein the ultrasound machine is implemented to generate the first ultrasound image as part of an ultrasound examination administered with the ultrasound system, and the circuit is implemented to make the determination during the ultrasound examination.

4. The ultrasound system as described in claim 1, wherein the classifier is implemented by the ultrasound machine and configured to generate a first classification label corresponding to the first type of electromagnetic emissions and a second classification label corresponding to the second type of electromagnetic emissions, wherein the first type corresponds to one of a narrowband electromagnetic emission, a harmonic electromagnetic emission, a broadband electromagnetic emission, a burst electromagnetic emission, or a random process electromagnetic emission, and the second type corresponds to other one of the narrowband electromagnetic emission, the harmonic electromagnetic emission, the broadband electromagnetic emission, the burst electromagnetic emission, or the random process electromagnetic emission.

5. The ultrasound system as described in claim 4, wherein the ultrasound machine is configured to determine, based on the classification and a list of sources and signatures of their electromagnetic emissions, a source of the electromagnetic emissions.

6. The ultrasound system as described in claim 1, further comprising at least one sensor configured to generate sensor data, wherein the circuit is implemented to make the determination based on the sensor data.

7. The ultrasound system as described in claim 6, wherein the at least one sensor includes an impedance sensor, and the sensor data includes an impedance.

8. The ultrasound system as described in claim 7, wherein the impedance sensor includes a current source configured to generate a current at a non-zero frequency selected based on frequency content of electromagnetic emissions, and the impedance is complex-valued.

9. The ultrasound system as described in claim 7, wherein the impedance sensor is implemented to generate the impedance from a first point to a ground point of the ultrasound system, the first point including at least one of a position on a ground spring clip and a position on a shield.

10. The ultrasound system as described in claim 6, wherein the at least one sensor includes impedance sensors located within the ultrasound machine and configured to generate an impedance matrix including impedances between the impedance sensors, and the circuit is implemented to make the determination based on the impedance matrix.

11. The ultrasound system as described in claim 10, wherein the circuit is implemented by the ultrasound machine and includes a neural network configured to:

generate, based on the impedance matrix, a probability that the first ultrasound image is corrupted by the noise process; and compare the probability to a threshold probability to make the determination.

12. The ultrasound system as described in claim 6, wherein the at least one sensor includes a light sensor, and the sensor data includes an amount of light.

13. The ultrasound system as described in claim 6, wherein the noise process includes electromagnetic emissions and the sensor data is indicative of the electromagnetic emissions, and the ultrasound machine is configured to determine, based on a property of the sensor data, a source of the electromagnetic emissions by correlating the property with properties known to be associated with the electromagnetic emissions.

14. The ultrasound system as described in claim 13, wherein the property includes at least one of a frequency content and a statistical classification.

15. The ultrasound system as described in claim 6, wherein the sensor data includes a number of open/close cycles of a display of the ultrasound machine.

16. A method implemented by an ultrasound system comprising an ultrasound scanner, an ultrasound machine coupled to the ultrasound scanner; and a circuit comprising a neural network and a classifier coupled to the neural network that is coupled to the ultrasound machine, the method comprising:

generating, by the ultrasound scanner, ultrasound data based on reflections of ultrasound signals transmitted by the ultrasound scanner;

generating, by the ultrasound machine, ultrasound images including a first ultrasound image and a second ultrasound image based on the ultrasound data;

determining, by the circuit, whether the first ultrasound image is corrupted by a noise process that includes electromagnetic emissions of a plurality of types including a first type and a second type; and determining, by the circuit, the electromagnetic emission as of the first type based on the first ultrasound image and the electromagnetic emissions as of the second type based on the second ultrasound image.

17. The method as described in claim 16, further comprising:

generating, by the neural network, based on the first ultrasound image, a probability that the first ultrasound image is corrupted by the electromagnetic emissions; and compare the probability to a threshold probability.

18. The method as described in claim 16, wherein the first ultrasound image is generated as part of an ultrasound examination administered with the ultrasound system, and said determining is performed during the ultrasound examination.

19. The method as described in claim 16, further comprising:

generating, by the classifier, a first classification label corresponding to the first type of electromagnetic emissions and a second classification label corresponding to the second type of electromagnetic emissions, wherein the first type corresponds to one of a narrowband electromagnetic emission, a harmonic electromagnetic emission, a broadband electromagnetic emission, a burst electromagnetic emission, or a random process electromagnetic emission, and the second type corresponds to other one of the narrowband electromagnetic emission, the harmonic electromagnetic emission, the broadband electromagnetic emission, the burst electromagnetic emission, or the random process electromagnetic emission.

20. The method as described in claim 16, wherein the ultrasound system comprises at least one sensor, and wherein the method further comprises:

generating, by the at least one sensor, sensor data; and determining, by the circuit whether the first ultrasound image is corrupted by a noise process based on the sensor data.

* * * * *